United States Patent
Gray et al.

(10) Patent No.: US 9,095,422 B2
(45) Date of Patent: Aug. 4, 2015

(54) METHOD AND STRUCTURE FOR NASAL DILATOR

(75) Inventors: David Gray, St. Paul, MN (US); Mark A. Litman, Edina, MN (US)

(73) Assignee: Liberman Distributing and Manufacturing Co., St. Paul, MN (US)

(*) Notice: Subject to any disclaimer, the term of this patent is extended or adjusted under 35 U.S.C. 154(b) by 427 days.

(21) Appl. No.: 13/175,024

(22) Filed: Jul. 1, 2011

(65) Prior Publication Data

US 2012/0004683 A1    Jan. 5, 2012

Related U.S. Application Data

(60) Provisional application No. 61/398,949, filed on Jul. 2, 2010.

(51) Int. Cl.
| | |
|---|---|
| *A61M 29/00* | (2006.01) |
| *A61F 5/08* | (2006.01) |
| *B29C 61/02* | (2006.01) |
| *B29C 47/00* | (2006.01) |
| *B29C 47/06* | (2006.01) |

(52) U.S. Cl.
CPC . *A61F 5/08* (2013.01); *B29C 61/02* (2013.01); *B29C 47/0021* (2013.01); *B29C 47/065* (2013.01)

(58) Field of Classification Search
CPC ....... A61F 5/08; A61F 5/56; A61F 2005/563; B29C 47/0021; B29C 47/065; B29C 61/02
See application file for complete search history.

(56) References Cited

U.S. PATENT DOCUMENTS

| | | | |
|---|---|---|---|
| 2,990,081 A | 6/1961 | De Neui et al. |
| 3,073,544 A | 1/1963 | Cirves et al. |
| 3,109,207 A | 11/1963 | Cooper |
| 3,132,204 A | 5/1964 | Giellerup |

(Continued)

FOREIGN PATENT DOCUMENTS

| | | |
|---|---|---|
| EP | 1866895 | 5/2010 |
| JP | H07-137190 A | 5/1995 |

(Continued)

OTHER PUBLICATIONS

"Fascinating Silicone Chemistry Corner Physical & Chemical Properties", obtained Aug. 13, 2011 and May 22, 2013, Dow Corning, http://www.dowcorning.com/content/discover/discoverchem/properties.aspx.

(Continued)

*Primary Examiner* — Katrina Stransky
*Assistant Examiner* — Kendra Obu
(74) *Attorney, Agent, or Firm* — Knowles Intellectual Property Strategies, LLC; Brent R. Bellows

(57) ABSTRACT

A nasal dilator and method of making nasal dilators are provided. The dilator may have
a composite base element of at least two regions, the base element having an outer surface and an inner surface,
the inner surface of the base element having a pressure-sensitive adhesive disposed thereon;
the base element further including a spring element which imparts return memory into the base element so that the base element returns towards a planar conformation during use. The spring element has elastic memory effected by differential properties in the at least two regions.

16 Claims, 7 Drawing Sheets

(56) References Cited

U.S. PATENT DOCUMENTS

| | | |
|---|---|---|
| 3,409,988 A | 11/1968 | Zelnick |
| 3,510,037 A | 5/1970 | Sharpe |
| 3,625,810 A | 12/1971 | Swartz |
| 3,718,495 A | 2/1973 | Tomita |
| 4,149,320 A | 4/1979 | Troyer et al. |
| 4,256,528 A | 3/1981 | Patterson |
| 4,313,991 A | 2/1982 | Lamb |
| 4,315,047 A | 2/1982 | Seabold et al. |
| 4,341,585 A | 7/1982 | Seabold et al. |
| 4,856,509 A | 8/1989 | Lemelson |
| 5,005,264 A | 4/1991 | Breen |
| 5,314,749 A | 5/1994 | Shah |
| 5,518,763 A | 5/1996 | Patnode et al. |
| 5,533,503 A | 7/1996 | Doubek et al. |
| 5,605,738 A | 2/1997 | McGinness et al. |
| 5,611,333 A | 3/1997 | Johnson |
| 5,653,224 A | 8/1997 | Johnson |
| 5,669,894 A | 9/1997 | Goldman et al. |
| 5,718,224 A | 2/1998 | Muchin |
| 5,725,814 A | 3/1998 | Harris |
| 5,837,789 A | 11/1998 | Stockhausen et al. |
| 5,890,486 A | 4/1999 | Mitra et al. |
| 5,953,826 A | 9/1999 | Goodyer et al. |
| 6,001,200 A | 12/1999 | Hibler |
| 6,029,658 A | 2/2000 | De Voss |
| 6,067,722 A | 5/2000 | Goodyer et al. |
| 6,098,616 A | 8/2000 | Lundy, Jr. et al. |
| 6,244,265 B1 | 6/2001 | Cronk et al. |
| 6,256,938 B1 | 7/2001 | Daton-Lovett |
| 6,372,341 B1 | 4/2002 | Jung et al. |
| 6,395,348 B1 | 5/2002 | O'Connor |
| 6,602,574 B1 | 8/2003 | Daton-Lovett |
| 6,631,714 B2 | 10/2003 | Von Duyke et al. |
| 6,680,097 B1 | 1/2004 | Amberger et al. |
| 6,694,970 B2 | 2/2004 | Spinelli et al. |
| 6,740,379 B1 | 5/2004 | Congard et al. |
| 6,769,429 B1 | 8/2004 | Benetti |
| 6,967,261 B1 | 11/2005 | Soerens et al. |
| 7,107,698 B2 | 9/2006 | Liao |
| 7,114,495 B2 | 10/2006 | Lockwood, Jr. |
| 7,462,753 B2 | 12/2008 | Ma et al. |
| 7,528,291 B2 | 5/2009 | Herfert et al. |
| 7,541,395 B2 | 6/2009 | Reimann et al. |
| 7,541,510 B2 | 6/2009 | Beaudry |
| 2001/0019764 A1 | 9/2001 | Bries et al. |
| 2002/0050318 A1 | 5/2002 | Donaldson et al. |
| 2003/0182878 A1 | 10/2003 | Warren |
| 2003/0230379 A1 | 12/2003 | Roubik |
| 2004/0077744 A1 | 4/2004 | Naylor et al. |
| 2005/0011665 A1 | 1/2005 | Youngers et al. |
| 2005/0027230 A1 * | 2/2005 | Beaudry .................. 602/54 |
| 2005/0074606 A1 | 4/2005 | Nishiyama et al. |
| 2007/0044801 A1 | 3/2007 | Mathis et al. |
| 2007/0141126 A1 | 6/2007 | Hudson et al. |
| 2008/0058858 A1 | 3/2008 | Smith |
| 2008/0131634 A1 | 6/2008 | Kiuchi et al. |
| 2009/0016209 A1 | 1/2009 | Ikeda et al. |
| 2009/0324883 A1 | 12/2009 | Gray et al. |

FOREIGN PATENT DOCUMENTS

| | | |
|---|---|---|
| JP | 2005-061212 | 3/2005 |
| JP | 2006-168005 A | 6/2006 |
| WO | WO 01/56777 | 8/2001 |
| WO | WO 2007056715 A2 * | 5/2007 |
| WO | WO2009132284 | 10/2009 |
| WO | WO 2009/158234 | 12/2009 |
| WO | WO 2012/003435 | 1/2012 |

OTHER PUBLICATIONS

"Si—Silicon", obtained Aug. 13, 2011, Ioffe Physical Technical Institute, http://www.ioffe.rssi.ru/SVA/NSM/Semicond/Si/mechanic.html.

Kebadze, et al., "Bistable prestressed shell structures" International Journal of Solids and Structures, vol. 41, 2004, pp. 2801-2820.

Mattioni, et al., "The application of residual stress tailoring of snapthrough composites for variable sweep wings" 47$^{th}$ AIAA/ASME/ASCE/AHS/ASC Structures, Structural Dynamics, and Materials Con-ference May 1-4, 2006, Newport, Rhode Island.

Satas, Donatas. "Handbook of Pressure Sensitive Adhesive Technology" 3rd ed., Warwick, RI: Satas & Associates, 1999, pp. 515-549.

International Search Report and Written Opinion from related PCT Application PCT/US2011/042780, Nov. 4, 2011.

* cited by examiner

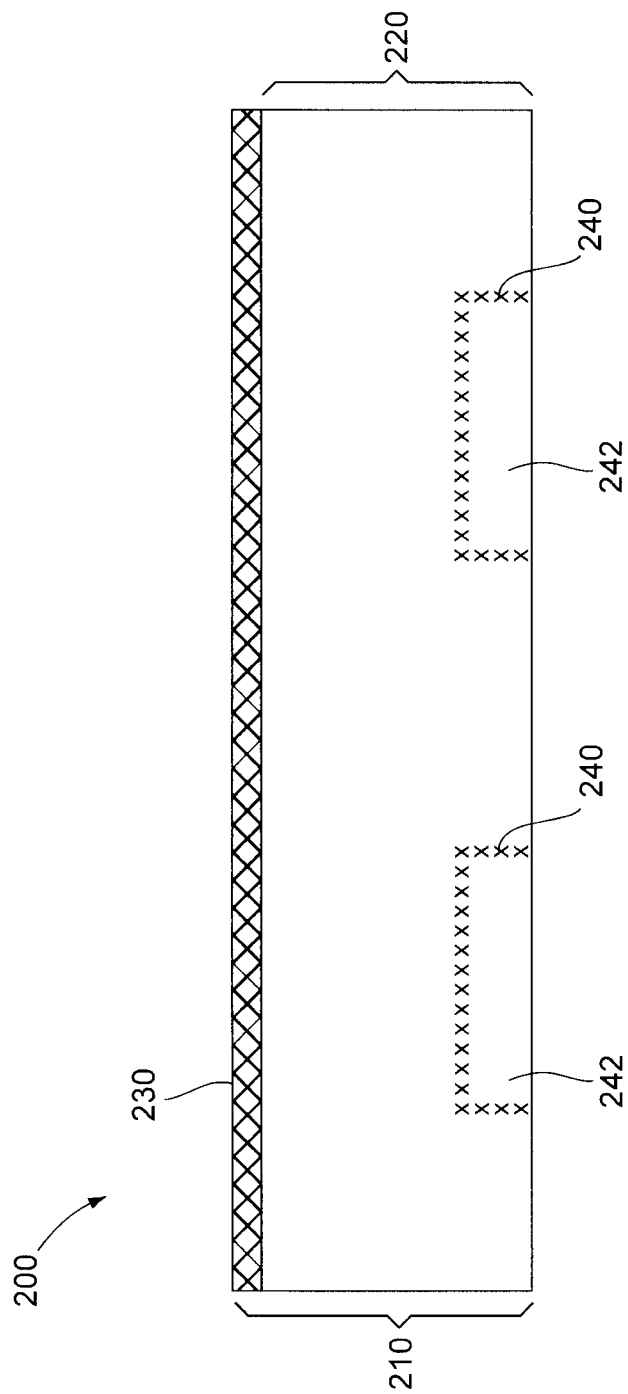

METHOD AND STRUCTURE FOR NASAL DILATOR

CROSS REFERENCE TO RELATED APPLICATION

This application claims the benefit of U.S. Provisional Application No. 61/398,949 filed on Jul. 2, 2010.

BACKGROUND OF THE INVENTION

1. Field of the Invention

The present invention relates to the field of nasal patches or nasal dilators that assist in keeping the exterior nasal passages open to assist in breathing and/or avoiding snoring. A process, structure, and composition of elements which assist in providing necessary or useful properties for the nasal dilator are provided.

2. Background of the Art

Nasal Dilators

Nasal dilators for opening nasal passages are known in the art. These nasal dilators are generally strips fabricated from multiple and separate components including a structural materials such as a woven material having an adhesive on one side for adhering to the nose and surrounding skin, a resilient member, and a backing. When adhered to the nose, the nasal dilators are designed to affect the opening of the nasal passages, providing relief for a wearer who may be experiencing difficulty in breathing or seeking to increase air flow through the nasal passages.

To accomplish this effect, prior art nasal dilators generally rely on the elastic or resilient member's ability to stabilize the nasal passages and reduce or prohibit nasal passage collapse or closing during breathing. When the strip is positioned across the nose, the resilient members operate as flexible, spring-like bands which desire to return to a more planar position, resulting in the lifting of the outer wall tissue of the nasal passage. As a result of this lifting, the collapsing or closing of the nasal passage openings during breathing is reduced.

As shown in FIG. 1, a typical prior art nasal dilator 100 is generally sized to fit across the nose of the wearer so as to engage the outer wall tissue of the left and right nasal passages. As shown in FIGS. 2-3, these nasal dilators 100 may include an elongated base substrate layer 30 having a pair of longitudinal sides, a pair of transverse ends and top and bottom surfaces thereon. The bottom surface of the base substrate layer 30 generally contains an adhesive layer 32 for permitting easy attachment to the wearer's skin. Nasal dilators of the prior art often utilize a separately manufactured resilient member 60 attached to the base substrate layer 30 during assembly. This resilient member 60 provides a gentle expanding force to the nasal wall tissue when the dilator is adhesively attached to the nose. Typically, the dilator 100 further includes a top or backing layer 40. The top or backing layer 40 and resilient member 60 are generally bonded to the substrate base layer 30, for example, by using pressure sensitive adhesive layers 42 and 62 during assembly.

In some embodiments, nasal dilators of the prior art further include, for example, an aromatic substance 50, such as a fragrance or aromatic stimulant or medication, disposed on a portion of the dilator so as to be inhaled through the nose of the wearer during breathing. Additionally, a substance that can be transdermally provided to the patient to effect a local biochemical result may also be included. The substance can be added to the bottom surface of the dilator 100, with, or without an aromatic substance.

Finally, a release liner or release paper strip 10, such as polymeric coated (e.g., silicone or fluorinated polymer) or wax coated kraft paper, is generally added over the pressure sensitive adhesive layer 32 prior to packaging the dilator 100 for sale.

Due to this design, a typical prior art nasal dilator requires using separate multiple components, manufacturing each component in a separate step, and then assembling the device in a multiple step process. Furthermore, the separate resilient member used in the typical nasal dilator tends add bulk to the nasal dilator.

U.S. Pat. No. 5,533,503 (Doubek at al.) describes a nasal dilator composed of a separate base substrate material, multiple separate resilient members comprised of plastic materials, separate flexible strips of adhesive materials, and a separate top or backing material. Accordingly, the manufacture of the nasal dilator is described as requiring the interface adhesive materials to be first laminated to the resilient band members, and then the top material laminated to the base material over the resilient band member.

U.S. Pat. No. 5,890,486 (Mitra) describes a multiple component nasal dilator having a separate base or substrate material, an intermediate segment, single or multiple resilient band members, adhesive strips, a thermal element, and a top or backing material. The resilient band members are described as being metal and/or plastic, and preferably industrial grade, oriented bi-axially oriented polyester that is approximately 2 mm to 8 mm wide and 0.25 mm thick. In alternative embodiments, the metal or plastic resilient band members are described as being formed within the base or top material through an extrusion process. The nasal dilators are described as being manufactured by bonding the base material to the top material, thereby encapsulating the resilient members, strips of adhesive materials, and thermal element in a unified structure.

U.S. Pat. No. 6,244,265 (Cronk et al.) describes a multiple component nasal dilator wherein separate substrate materials, resilient members, and backing materials are adhesively joined together as they are fed into an overlapping position in a die or roller. Adhesive layers are used to join the backing layer, resilient member and elongated substrate together prior to die-cutting to form the final periphery of the dilator. The described nasal dilators further include medications and/or fragrances disposed in or on the backing and/or substrate material.

U.S. Pat. No. 6,769,429 (Benetti) discloses a nasal dilation device that includes a single, integral strip of flexible resilient material having a central portion for positioning over and in engagement with the top of an individual nose and opposed end portions including independently flexible upper and lower finger elements diverging from one another. The resilient material is described as a single clear plastic material in a thickness range of from about 0.2 mm to about 0.6 mm. Separate adhesive tape elements overlie the end portions for releasably securing the end portion to opposed sides of the individual's nose.

U.S. Pat. No. 6,694,970 (Spinelli et al.) describes a multi-component nasal dilator that includes a base material having an adhesive on one surface for applying the strip across a human nose and at least one biasing or resilient member attached or embedded in the strip, wherein the biasing or resilient member is fabricated from a material, preferably metal, which exhibits a shape memory effect upon being heated toward a human body temperature, preferably by the heat of the nose. The biasing or resilient member is described as having a shape upon being heated toward the human body temperature that results in the material reverting to austenite and then recovering its previous shape, which biases the nasal passages of the human nose toward an open position.

U.S. Pat. No. 7,114,495 (Lockwood) describes a multiple component, multi-layer nasal dilator capable of introducing separating stresses in nasal outer wall tissues having a resilient band member, which is symmetrical with respect to a centerline of the truss that is perpendicular to the long axis of the truss, with a spring rate which continuously diminishes from the centerline to the end surfaces. An adhesive on the end surfaces adhesively engages exposed surfaces of nasal outer wall tissues sufficiently to keep the truss attached to the nasal wall surfaces while subjecting them to the restoring forces. The nasal dilator also includes a top or backing layer, and a cushion layer designed to prevent direct contact between the resilient band member and the skin of the user.

SUMMARY OF THE INVENTION

The present invention is a nasal dilator made from a composite material that provides shape memory and resiliency, wherein the nasal dilator comprises one of the following three embodiments: 1) a composite base element comprising at least two distinct regions; 2) a coextruded composite base element comprising at least two materials; or 3) a laminate composite base element comprising at least two materials; wherein at least one of the materials or distinct regions has at least one differing chemical or physical property from the other, and the interaction of the at least two materials or distinct regions creates a spring-like element in the base element which imparts resiliency into the base element and provides the base element with return memory properties towards a planar conformation. In a preferred embodiment, the composite material is the only structural material used in the nasal dilator, and is not part of a type of multicomponent structure as described in the prior art in the Background of the Invention. The use of composite material can allow the device to be lighter and/or thinner than multicomponent devices, for user comfort, and ease of use.

In another embodiment, the composite material is used in combination with one or more additional materials to provide desirable properties.

The term "composite" is used to describe an element comprising two or more chemically or physically differing materials or two or more chemically or physically differing regions. Preferably in a composite, at least one of the different materials is a polymeric material, and more preferably a polymeric material having semicrystallinity.

The term "spring-like element" or "spring element" is used to describe the tension providing element or elastic memory providing element in the nasal dilator. The spring element encompasses any region, area, article, layer, or layers within the base element, in this case within the composite, that provides forces within the nasal dilator that causes a lifting tension of the nasal dilator away from the nasal passages. The elastic memory of the spring element provides its spring-like nature. The spring element can be induced or formed by the interaction of two or more materials or regions having differing characteristics. Because the resiliency of the base element, in this case the composite, provides the necessary lift to reduce or prohibit nasal passage collapse or closing during use, the present invention may effectively eliminate the need for a separate resilient member in the dilator, and can reduce the amount and thickness of the materials used to manufacture the nasal dilator and/or simplify the manufacturing process by reducing the number of steps required to manufacture the nasal dilator.

The term polymer includes the possibility of copolymers and/or cross-linked polymers or copolymers and polymers having semicrystalline internal structure.

The nasal dilator of the present invention includes a composite base element and an adhesive disposed on one-side thereof for adhering the nasal dilator to the user's nose, which together form the nasal dilator. The composite base element can be formed from a single material having different physical characteristics across two or more regions, or from two or more materials preferably co-formed during manufacture. In certain embodiments, the composite base element has one or more materials having spring elements physically or chemically induced at particular regions on the base element, resulting in a base element with different physical characteristics across two or more regions. In certain embodiments, the composite base element is co-formed through a co-extrusion process of two different materials. In certain embodiments, the composite base element is co-formed by laminating two different materials in a lamination process.

The base element has an elasticity built into it that will lift opposed sides of the nose by a spring or elastic action moving the base element from a curved shape over the nose towards a more linear form while the nasal dilator remains adhered to the nose. By using a composite that acts as both a base substrate and a resilient member, manufacturing steps and/or materials previously used in the manufacture of nasal dilators can be eliminated, costs reduced, manufacture simplified and properties tailored.

The interaction or separate actions of the materials used to form the composite base element impart the appropriate strength, flexibility and spring action required for the material to act as a nasal dilator. For example, a secure retention of pressure-sensitive adhesive is needed in the outer surface, while a relatively strong straightening elastic memory is needed to cause the essential lifting action in the performance of the nasal dilator. Many commercial dilators have separate metal or hard plastic fibers, rods or filament inserts that act as resilient members that must be carefully constructed and placed within the layers of the nasal dilators, resulting in a construction that can be complex, costly, and inefficient. By creating a spring element at or along the interface of chemically or physically differing materials, the use of separate metal or hard plastic inserts may be avoided.

The present technology allows for simultaneous construction of all components of the composite nasal dilator and subsequent or simultaneous application of the pressure-sensitive adhesive layer. In one aspect of the invention, a continuous process for manufacturing nasal dilators is provided. One underlying element of technology described herein includes as a preferred embodiment a process of forming the composite nasal dilator by co-extrusion of two or more materials with differing characteristics, including different synthetic polymeric or composite materials, in appropriate orientation and layering that provides the ultimate desirable spring element properties. By differing characteristics, it can include either differences merely by the fact of using differing polymers (for example polyester, polyacrylates, polyolefins such as polypropylene (including high density polypropylene or polyethylene, copolymers thereof and the like), or materials of differing characteristics or qualities whether the same or different polymer or copolymer, such as, but not intended to be limited to, density, quality, response to external conditions, chemical composition, crystallinity, molecular weight, crosslinking, glass transition temperature, thermoplastic vs. thermoset, morphology, heat shrink, cold shrink, expansion, flexibility, hardness, elasticity, shape memory, stiffness, and the like. Some desirable properties (e.g., stiffness and memory) may be developed, activated or made latent in a single co-extrusion step by controlling the properties, compositions and additives in the various coextruded elements. Similarly, the composite base element can be derived through a lamination of two or more materials with differing properties in an appropriate layering and orientation to provide the desirable characteristics. The co-formed composite base element materials act in concert to allow for sufficient flexibility in the composite nasal dilator structure to conform to the curvature over a human nose, and then to provide such sufficient elastic memory in attempting to return towards a planar orientation of the nasal dilator so as to lift outer surfaces of the nose and dilate nasal passages within by the lifting action.

In certain embodiments, the composite nasal dilator may include:
  a) a composite base element comprising one or more materials having an outer surface and an inner surface;
  b) the inner surface having a skin-compatible or hypoallergenic or non-irritating adhering material, which can be a pressure sensitive material, thereon;
  c) wherein the composite base element has a spring element that provides tension, elastic memory and/or stiffness to the base element when the base element is transitioned from a planar to a non-planar state during use; and
wherein the spring element is formed through the interaction of at least two materials or two distinct regions in the base element, the spring element imparting resiliency into the base element and providing the base element with return memory properties towards a planar conformation during use.

In one embodiment, the spring element of the base element is induced by physically or chemically altering at least one region in the base element. The chemical or physical alteration creates at least two distinct regions within the base element, whose interaction induces a spring element. In one embodiment, the spring element is formed by physically or chemically treating the base element to alter its elastic memory. In one embodiment, the spring element is formed by heating certain regions within the base element. In one embodiment, the base element is comprised of at least one shrink material or shrink film.

In one embodiment, the spring element in the base element may be formed through the interaction of two or more materials with different native chemical or physical properties, which elements are co-formed during an extrusion process or lamination process. In one embodiment, the spring element is derived by co-forming two or more materials with different coefficients of expansion. In an alternative embodiment, the spring element is derived by co-forming two or more materials with different rates of contraction upon cooling. The differing co-efficient of expansion or contraction upon cooling properties act to create a tension or stiffness at the interface of the differing materials within the base element, resulting in the base element having an elastic memory when the base element is placed upon the user's nose. This elastic memory is not substantially altered (e.g., the tension may preferably not increase by more than 5%) upon ambient heating, as by body temperature increasing the base temperature of the device from 20° C to 37° C. In one embodiment, the spring element of the composite base element is induced by using at least two materials with differing shrink properties when exposed to heat, wherein the material with the greater shrinkage creates tension along the interface of the two materials. In one embodiment, at least one of the materials of the composite base element is a shrink film.

In one embodiment, the composite base element is formed by co-extruding two or more materials, wherein the interaction between the two or more materials at or about their interface in the base element induces a shape memory effect and/or spring element.

In certain embodiments, differential changes in the materials or regions of the base element in response to physical conditions, such as heating, cooling, the loss of solvent, the absorption of solvent, the loss of moisture, or the absorption of moisture may induce a change in shape through a controlled differential bending along the spring element, which can provide the nasal dilator with a controlled uplifting spring force when placed on the user's nose. In certain embodiments the change in shape may cause controlled differential bending along the spring element resulting in the inner surface of the base element changing to a concave shape that will secure itself to the nose of the wearer by the adhesive, with controlled uplifting spring force. In certain embodiments, the change in shape may cause the base element to bend in a direction opposite its position during use, creating control uplifting spring force on the nostrils during use. In certain embodiments, the change in shape may result in the development of a curvature along the longitudinal width of the nasal dilator, creating uplifting spring force during use.

In certain embodiments, once applied to the nose, the spring force of the base element may or may not be adjusted by body temperature, but may be adjusted by application of more or a different solvent, cooling, or the loss or absorption of moisture. In certain embodiments, the differing physical characteristics of the materials or regions of the base element imparting the spring element may be present initially after formation of the base element or may be latent properties that can be activated after formation of the base element, including either before use of the nasal dilator or during use of the nasal dilator. In a preferred embodiment, the spring element is induced in the base element by exposing the base element to sufficient heat to cause a significant alteration or inducement of lifting tension away from the nasal passages, wherein at least one material of the base element, or alternatively one region of the base element, differentially shrinks or expands in response to the heat, creating the spring element. The changes in properties should create a lifting force of at least 2 grams, preferably at least 5 grams on each side of the nose. In one embodiment, the base element is exposed to heat prior to application to the nose of a user in order to create the spring element. In one embodiment, the base element is exposed to heat prior to packing in order to create the spring element.

When the two materials used to create the spring element have differential shrink properties, differential contraction properties, or differential expansion properties, the application of thermal energy (by conductive or convective heating, IR radiation, and the like) will cause the two materials to shrink, contract, and/or expand at different rates. Particularly when there is a persistent or permanent change caused by shrinkage, contraction, or expansion (e.g., as with a heat shrink material being one of the components, layers or films), the differential in dimensions caused by shrinkage, contraction, and/or expansion causes the combined layers to arc or curl, with the "shorter" or greater shrinking component being on the concave side of the arc and the "longer" or less shrinking component being on the convex side of the arc. The changes in the properties of the two components may also act by the "longer" component on the exterior or convex side shrinking (thereby reducing differences and flattening the composite) or by the "shorter" component on the interior or concave side expanding (thereby reducing differences and flattening the composite). The arc can be created along the longitudinal length or, if desired, width of the nasal dilator, or both. It is preferred that the thermal treatment create a permanent memory of the dimensional change as by heat shrinkage, heat contraction, or heat relaxation of the material, as is known to occur in the classes of shrink materials discussed and described herein. The extent or degree of arc or curl can be controlled so that the appropriate tension, elastic memory and/or stiffness are imparted to the base element when the base element is transitioned from a planar to a non-planar state during use.

There are various methodologies of forming these composite nasal dilators, which may include steps such as: a) creating a composite base element having an outer surface and an inner surface, wherein the composite base material is comprised of at least two materials or two regions differing in at least one chemical or physical characteristic; and b) inducing a spring element in the base element through the interaction of the at least two materials or two regions. In one embodiment, the induction of the spring element results in the deformation of the base element from a linear shape so that the base element also deforms from a planar shape. In certain embodiments, the change in shape may cause controlled differential bending along the spring element resulting in the inner surface of the base element changing to a concave shape that will secure itself to the nose of the wearer by the adhesive, with controlled uplifting spring force provided during use. In certain embodiments, the change in shape may cause the base element to create tension in a direction opposite its position during use, creating control uplifting spring force on the nostrils during use. In certain embodiments, the change in shape may result in the development of a curvature along the longitudinal width of the nasal dilator, creating uplifting spring force during use.

In certain embodiments, the nasal dilator may include a base element having a spring element derived from at least one physically or chemically altered region of a base element. In certain embodiments, the spring element is formed by physically or chemically treating the base element to alter its elastic memory prior to application to the nose or after application to the nose. For example, by heat-scoring lines on one side of the base element, the scored surface may shrink or expand, as desired, creating spring elements and causing the curvature of the base element to form the spring upon use. The heat-scoring may be done and then a chemical or thermal process performed to take advantage of the difference in local properties created by the scoring, resulting in the spring properties to becoming active. In certain embodiments, after the spring element is formed through a first chemical or physical process, a second chemical or physical process may be applied to the base element to cause a change in shape along the spring element so that the inner surface of the base element is a concave shape. In certain embodiments, the change in shape may cause the base element to create tension in a direction opposite its position during use, creating control uplifting spring force on the nostrils during use. In certain embodiments, the change in shape may result in the development of a curvature along the longitudinal width of the nasal dilator, creating uplifting spring force during use.

In certain embodiments, the spring element is formed in the composite base element by co-extrusion of two materials with different physical or chemical characteristics that cause, or enable further treatment to cause, a change in shape. For example, the different physical characteristics may be different coefficients of thermal expansion, different coefficients of shrinkage after co-extrusion, different swelling or shrinkage rates of the differing materials due to a solvent or more than one solvent being added to or dried out of the co-extruded materials. In certain embodiments, at least one material has a three-dimensional shape with an elastic memory.

In certain embodiments, the spring element is formed in the composite base element through a lamination of two materials with different physical or chemical characteristics that cause, or enable further treatment to cause, a change in shape. For example, the different physical characteristics may be different coefficients of thermal expansion, different coefficients of shrinkage induced after lamination, different changes in crystallinity and orientation (causing changes in the physical length of molecules and polymer chains), different swelling or shrinkage rates of the differing materials due to a solvent or more than one solvent being added to or dried out of the laminated materials. In certain embodiments, at least one of the materials has a three-dimensional shape with an elastic memory. In one embodiment, the composite base element is comprised of at least one shrink material. In one embodiment, at least one of the materials is a shrink film. In one embodiment, the shrink film is laminated on a second material, wherein the second material has an adhesive for adhering to a user's nose, which can be a pressure sensitive adhesive, disposed on a side opposite the shrink film. In one embodiment, the composite base material is comprised of a first material comprising a medical grade cloth material and a second material comprising a shrink material. In one embodiment, the shrink material is a polyolefin. In one embodiment, the shrink material is a polyolefin material such as a polyethylene or a polypropylene shrink film.

In one aspect of the invention, a continuous process for manufacturing nasal dilators is provided comprising providing a base element, wherein the base element is formed by: (a) extruding a first material having a first surface and a second surface from a first extrusion die or co-extrusion die, the first surface and second surface having differential properties that cause or enable curling tension to be formed or later created in the base element; and/or (b) extruding a second material having a first surface and a second surface from a co-extrusion die, or separated slot coating position downstream from the first extrusion or coextrusion die, wherein the first material and second material or the first surface and second surface co-form the base element, the second material or second surface having different chemical or physical properties than the first material or first surface, wherein the interaction of the first material and second material provides a spring-like function or element to the base element. Differential properties in the surfaces of even a chemically homogeneous material may be formed by differential treatment of the surfaces in or after the extrusion process (e.g., different cooling temperatures and/or cooling rates on the surfaces, different heating processes on the opposed surfaces with IR heaters, or different crystalline state or degree imposition on the surfaces by thermal or irradiation treatments such as pulsed excimer laser treatment, or a combination thereof). In one embodiment, the second material is extruded into or on only a portion of one surface of the first material. It would be preferred to have the second material asymmetric within the combination (e.g., totally on one side of the combined materials or slightly off-centered within the combined materials) so that the direction and degree of subsequent curvature and tension in the elastic memory can be better controlled. In certain embodiments, the interaction of the first material and the second material results in the base element having an elastic memory or a latent elastic memory that can be changed by additional processing such as heat, irradiation or solvent. In certain embodiments, the second material has a three-dimensional shape with an elastic memory. In certain embodiments, the first or second material shrinks or expands when exposed to heat. In one embodiment, the process further includes exposing the composite base element to heat in order to induce shrinkage in the first or second material, thereby creating tension between the two materials which provides the spring element of the base element. In certain embodiments, the process further includes extruding or slot coating a third material onto a surface of the first material opposite the second material, wherein the third material comprises a pressure sensitive adhesive. In certain embodiments, the process can further include laminating a release paper strip, such as silicone or wax coated kraft paper, over the adhesive, which can be a pressure sensitive adhesive layer. In certain embodiments, more than one nasal dilator can be formed in a continuous process.

One benefit of forming these structures by extrusion and or extrusion plus slot-coating of the adhesive on the extruded substrate is the ability to work on a continuous process on a single continuous line of manufacturing apparatus. The base and underlying layers of structure in the device can thus be mass produced on a single web-handling device, and the sheet converted into appropriately sized individual nasal dilator elements.

In one aspect of the invention, a continuous process for manufacturing nasal dilators is provided comprising providing a composite base element by: (a) providing a first material having a first surface and a second surface; (b) laminating a second material having a first surface and a second surface on to at least one portion of the first material (the lamination being effected with adhesive or without adhesive, as by direct fusion of the layers together), wherein the first material and second material co-form the base element, the second material having different chemical or physical properties than the first material, and wherein the interaction of the first material and second material creates a spring element to the base element. In one embodiment, the second material is laminated onto only one portion of one surface of the first material. In certain embodiments, the interaction of the first material and the second material results in the base element having an elastic memory. In certain embodiments, the second material has a three-dimensional shape with an elastic memory. In one embodiment, the process further includes exposing the base element to a physical or chemical treatment, wherein the differential response to the treatment by the two materials induces the spring element. In certain embodiments, the physical or chemical treatment may include exposure to heat, exposure to cold, exposure to dryness, exposure to moisture, exposure to a chemical or solvent, exposure to thermal or irradiation treatment (such as pulsed excimer laser treatment), or any combination thereof. In certain embodiments, the first or second material shrinks when exposed to heat. In one embodiment, the process further includes exposing the composite base element to heat in order to induce shrinkage in the first or second material, thereby creating tension between the two materials which provides the spring element of the base element. In one embodiment, the composite base element is comprised of at least one shrink material. In one embodiment, the composite base material is comprised of a first material comprising a medical grade cloth material and a second material comprising a shrink material. In one embodiment, the shrink material is a polyolefin. In one embodiment, the shrink material is a polyethylene or a polypropylene shrink film. In certain embodiments, the process further includes disposing on a surface of the base element a pressure sensitive adhesive. In one embodiment, the process includes laminating a release paper strip, such as silicone or wax coated kraft paper, over the pressure sensitive adhesive layer. In certain embodiments, more than one nasal dilator can be formed in a continuous process.

In one embodiment, the composite base element produced as an extrudate or laminate is die-cut and formed into a roll.

These and other methodologies may be used to provide the spring element.

DESCRIPTION OF THE FIGURES

FIG. 4 shows a cross-sectional view of an exemplary composite nasal dilator wherein the spring element is derived within certain regions of the base element by physically or chemically altering the base element to create specified spring elements within the base element.

DETAILED DESCRIPTION OF THE INVENTION

Figure 1:
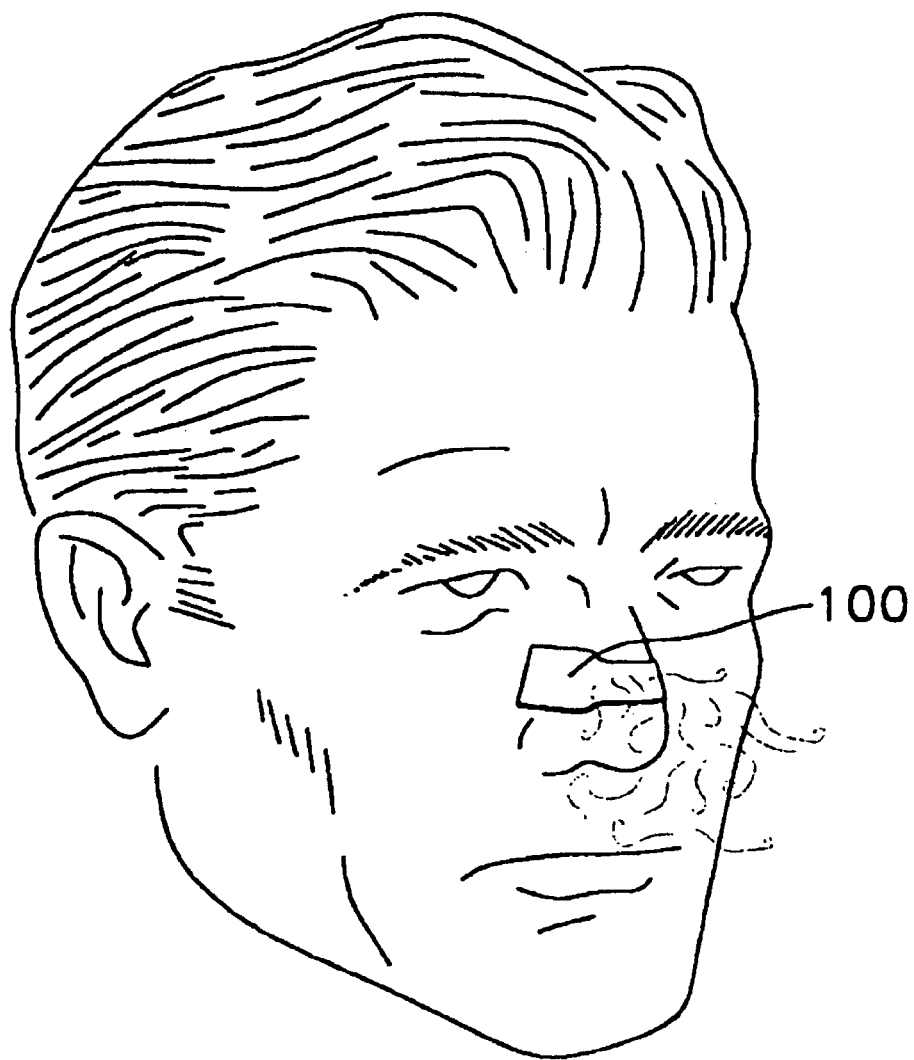
FIG. 1 shows a typical nasal dilator attached to a person, including structures of the prior art.
Figure 2:
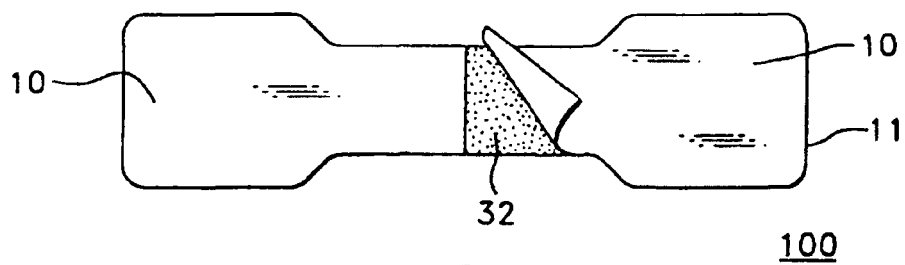
FIG. 2 shows the construction of a typical nasal dilator according to the prior art.
Figure 3:
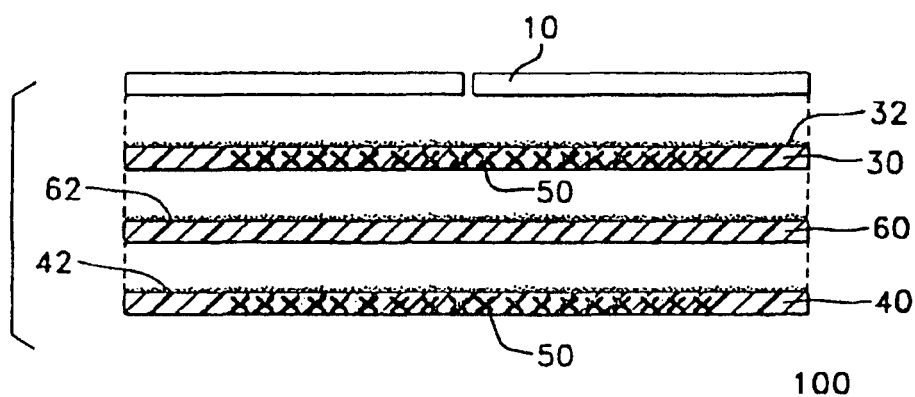
FIG. 3 shows a cross-sectional view of a standard nasal dilator according to the prior art.

The current invention is directed to nasal dilators and methods of manufacturing nasal dilators. In particular, the current invention is directed to nasal dilators having a composite base element that provides resiliency to the nasal dilator, allowing the base element to be flexible and providing the base element with return memory properties towards a planar conformation.

In one aspect of the present invention, the nasal dilator includes:
  a) a composite base element having an outer surface and an inner surface;
  b) the inner surface having a (e.g., skin compatible) pressure-sensitive adhesive thereon;
  c) the composite base element having induced therein a spring element that provides tension, elastic memory, and/or stiffness to the base element when the base element is transitioned from a planar to a non-planar state; and wherein the spring element is formed through the interaction of at least two materials, opposed surfaces of the base element or two distinct regions providing the base element with return memory properties towards a planar conformation.

Referring now to FIGS. 4-7, a cross-section of exemplary composite nasal dilators are illustrated therein, the nasal dilator being generally referred to by reference numeral 200. The nasal dilator 200 comprises a base layer 210 comprised of a base element 220 and an adhesive layer 230, the adhesive layer 230 being disposed on the side of the base element 220 that is to be adhered to the user's nose. The base element 220 is comprised of a composite material having two differing materials or regions, wherein the interaction of the differing materials or regions imparts at least one spring element 240 that provides the base element with return memory properties towards a planar conformation.

The base element 220 may include one or more thin, flexible materials suitable for use in nasal dilators. Preferably, the base element 220 is breathable, allowing airflow and/or moisture flow, and is selected to maximize comfort. The base element 220 may include, for example, porous or microporous polymer film, a fabric materials such as one or more woven or non-woven fabric layers, such as non-woven, polyester fabric with a strengthening mesh therein, or a combination thereof. One example is a fabric produced by DuPont E. I. de Nemours & Co., Inc. under the trademark Sontara®. Alternatively, the base element 220 may include, for example, one or more thermoplastic woven or non-woven fabrics, such as polyethylene or polypropylene (which can be spun-bonded), or a combination thereof. In other alternatives, the base element 220 may for example include one or more materials such as paper, cloth, including medical grade cloth, vinyl, polypropylene, including oriented polypropylene such a MOPP and BOPP, polyester, polyethylene, including LDPE, LLDPE, MDPE, HMWPE, and HDPE, more generally polyolefin, polyethylene terephthalate, glycolised polyethylene terephthalate (PETG), acrylonitrile butadiene styrene, polycarbonate, polyvinyl chloride, cellophane, cellulose, cellulose acetate, block co-polymers such as styreneisoprene, butadiene or thylene-butylene/styrene (SIS, SBS, or SEBS), polyurethane, ethylene copolymers such as ethylene vinyl acetates, ethylene/propylene copolymer elastomers or ethylene/propylene/diene terpolymer, nylon, crepe, flat back, a foil, rayon, a polyvinyl derivative, polyamides, cuproammonium cellulose, wool, silk, jute, hemp, cotton, linen, sisal, ramie, polystyrene, polyurethane, polyvinylidene chloride, saponified ethylene-vinyl acetate copolymer, linoleum, acrylics, natural rubber, reclaimed rubber, synthetic rubber, thermoplastic resin films, biodegradable resins such as polylactic acid and polyhydroxyalkanoates, polybutylene terephthalate, polyethylene naphthalate, polybutylene terephthalate, polyamide, polyimide, other resins, other thinfilms, or combinations thereof.

In certain embodiments the base element 220 is formed by using two physically or chemically differing materials, wherein the interaction of the differing materials in relation to each other imparts a spring element to the base element 220, providing the desired resiliency in the nasal dilator 200. In certain embodiments, the base element 220 will include two or more materials, wherein the interactions of the two or more materials impart or induce a spring element 240 within or across the base element 220. In certain embodiments, the different materials may have different crystallinity, allowing heat in the layers to cause changes in shape memory, stiffness, and/or flexibility that differentially effects one material compared to the other. Different crystalline properties of the materials may be provided by at least one of: different temperatures used during extrusion or lamination or subsequent to extrusion or lamination; different levels or types of solvents; different radiation exposure during or after extrusion or lamination such as infrared radiation, pulsed laser, or ultraviolet radiation; different levels of crosslinking agents; different levels of flexibilizers; or different levels of crystallinity promoters. Different levels may also include zero content in one of the materials.

In certain embodiments, the spring element 240 can be induced during the co-extrusion of two materials by using different shapes and orientations of co-extrusion heads or slots which may impose greater planarity or greater curvature between the at least two materials.

In certain embodiments, the base element 220 is comprised of at least two materials, wherein at least one of the materials shrinks or expands disproportionately compared to at least one other material used in the base element 220. In certain embodiments, the base element 220 is comprised of at least two materials, wherein at least one of the materials shrinks, contracts, or expands disproportionately along its longitudinal length when compared to at least one other material used in the base element 220. In one embodiment, the base element 220 is comprised of two or more materials, wherein at least one of the materials is a shrink film which shrinks disproportionately when compared to at least one other material used in the base element 220. In one embodiment, the base element 220 is comprised of two or more materials, wherein at least one of the materials is a shrink material which shrinks along its longitudinal length in a disproportionate ratio compared to at least one other material used in the base element 220. In certain embodiments, the base element 220 is comprised of at least two materials or one material having opposed surfaces treated to create a differential in bending torque and/or elastic memory in the base element, wherein at least one of the materials or surfaces shrinks, contracts, or expands when exposed to heat in a disproportionate ratio compared to at least one other material used in the base element 220. Upon exposure to heat, the shrinkage, contraction, or expansion of the material creates tension between it and at least one other material within or across the base element 220, imparting a resiliency on the base element 220. In certain embodiments, the at least one material has a three-dimensional shape with an elastic memory.

Shrink materials useful for the present invention may include conventionally known materials prepared from one or more resins that shrink or contract upon heating. Such materials can include, for example, polymers and/or semicrystalline polymers such as one or more of the following: polyolefin (including cyclic polyolefin), including polypropylene and polyethylene; polyvinyl chloride; polyesters; polystyrenes; polyvinylidene chlorides; polyethylene terephthalate; polynorbornene; polyimide; polyamide; polyurethane; polystyrene; polyvinylidene chloride; polyvinyl chloride; or a combination or combinations thereof. In certain embodiments, the shrink material may comprise a shrink film. Shrink films can include, for example, uniaxially and biaxially stretched shrink films. Shrink films can include, for example, films, including monolayer and multilayer laminated films, made from one or more of the resins identified above. For example, shrink films can include: polyolefin shrink films, such as polyethylene and polypropylene shrink films (including oriented polypropylenes such as BOPP and MOPP); polyurethane shrink films; and polyvinyl chloride shrink films. Monolayer polyolefin shrink films include cross-linked and uncross-linked oriented polyethylene, oriented polypropylene, polyurethane, and oriented ethylene-propylene copolymers. Monolayer polyvinyl chloride ("PVC") shrink films involve a variety of PVC formulations. Shrink films useful in the present invention may include shrink films commercially available from: Bemis Co. Inc. such as Clysar® ABL polymer, Clysar® polymer AFG, Clysar® EZ polymer, Clysar® HPG polymer, Clysar® LEG polymer, Clysar® LLG polymer, Clysar® ShrinkBox polymer, and Clysar® VHG polymer; Toyobo Co., such as Space Clean 55630 polymer; Intertape Polymer Group, such as Exlfilm® polymer; Reynolds Packaging LLC such as Reynolon® polymer, Reynolon® Plus polymer and PVC shrink films; Syfan USA, Corp. such as Sytec® shrink films; Mitsubishi Polyester Film; Gunze Ltd. such as Fancy Wrap® polymer; Toray Industries Ltd. such as Toradan® polymer and Lumirror® polymer; JSR Corp. such as Arton® polymer; Nippon Zeon Co. such as Zeonore® polymer; and the like In one embodiment, the shrink film is a polyolefin shrink film. In one embodiment, the shrink film is a polypropylene. Upon exposure to heat, a shrink material will either shrink or, if restrained, create shrink tension within the base element 220, creating a tension along and elasticity along the spring element 240. This heat reaction is generally activated when the shrink material is exposed to heat.

The nasal dilators of the present invention further include a pressure sensitive adhesive 230 disposed on the inner surface of the base element 220. The pressure sensitive adhesive 230 adheres the nasal dilator 200 to the user's nose. The pressure sensitive adhesive may include any releasable adhesive or releasable tenacious components to affect pressure-sensitivity. Pressure sensitive adhesives suitable for nasal dilators are well known and include water-based pressure-sensitive adhesives, such as acrylate adhesives, thermoplastics "hot melt" adhesives, two-sided adhesive tape, elastomer-based adhesives, and acrylic adhesives. Examples include polyacrylate adhesive, and polyvinylethyl ether blend adhesives.

Additional elements of the nasal dilator contemplated in the current invention may include a release film or release paper strip that can be added over the pressure sensitive adhesive layer 230 prior to packaging.

In certain embodiments, the composite base element 220 is composed of one or more materials extruded from an extrusion die. In certain embodiments, the base element 220 is composed of at least two materials formed during a lamination.

The base element 220 has at least one spring element 240 induced therein. In one embodiment, the spring element 240 is derived from physically or chemically altering at least one region of the base element 220 in order to alter its elastic memory. In one embodiment, the base element 220 is heated in one or more locations in order to shrink or expand the base element to cause a curvature, wherein the induced curvature creates the spring element 240. In one embodiment, heat-scoring lines are provided on one side of the base element 220, and chemical, radiation (e.g., pulsed excimer laser) or thermal processing is subsequently performed to take advantage of the difference in local properties created by the scoring, imparting a spring element 240 within or across the base element 220. In certain embodiments, after the composite base element 220 is formed, a subsequent chemical or physical process may be applied to the base element 220 to cause a change in shape of the base element 220, imparting a spring element 240 across the base element 220 so that the inner surface of the base element 220 is transformed into a concave shape. In certain embodiments, the change in shape may cause the base element 220 to create tension in a direction opposite its position during use, creating control uplifting spring force on the nostrils during use. In certain embodiments, the change in shape may cause the base element 220 to develop a curvature along the longitudinal width of the nasal dilator, creating uplifting spring force during use.

For example, the elastic memory properties of the spring element 240 may be induced in or created on the base element 220 by using at least one material in the base element 220 which reacts to a physical or chemical condition in a differential manner when compared to at least one other material used in the base element 220. In this way, the positioning or layering of the different materials, and the effects of the induced spring element 240 can be controlled by selectively orienting the materials in the base element 220 in such a way so as to take advantage of the differential response to the chemical or physical condition. In one embodiment, the spring element 240 is induced by co-forming two materials with different coefficients of expansion. In an alternative embodiment, the spring element 240 is induced by co-forming two or more materials with different rates of contraction upon cooling. In still another embodiment, the spring element 240 is induced by co-forming two or more materials with differing resistance to force, wherein the resistance of one material to force acts to induce a strain or tension on the nasal dilator in the direction of the planar form when the nasal dilator is placed across the user's nose. In another embodiment, the spring element 240 is induced by co-forming two or more materials with different rates of shrinkage when exposed to heat.

Figure 4A:
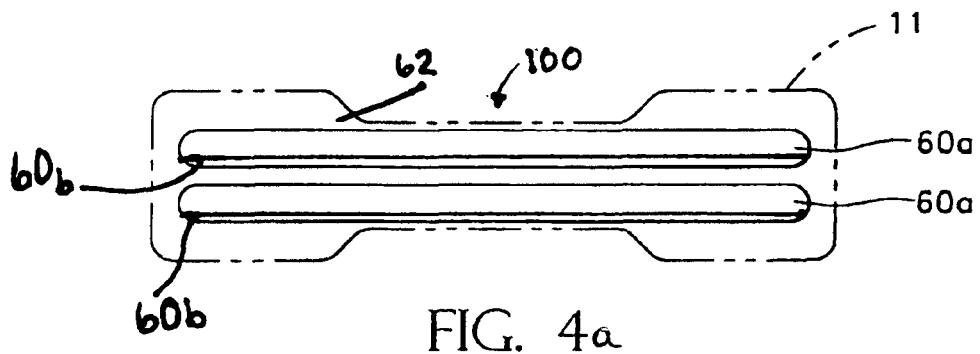
FIG. 4A is a top view of a nasal dilator.

As shown in FIG. 4, the spring element 240 providing the nasal dilator 200 with flexibility and return memory properties towards a planar conformation may be imparted within certain regions of the base element 220. In one embodiment, the spring element 240 is induced by chemically or physically treating the base element 220 as described above, for example by heat scoring, along particular areas 242 of the base element 220 to impart the spring elements 240 of the base element 220 wherein an induced spring element effect is desired.

Figure 5:
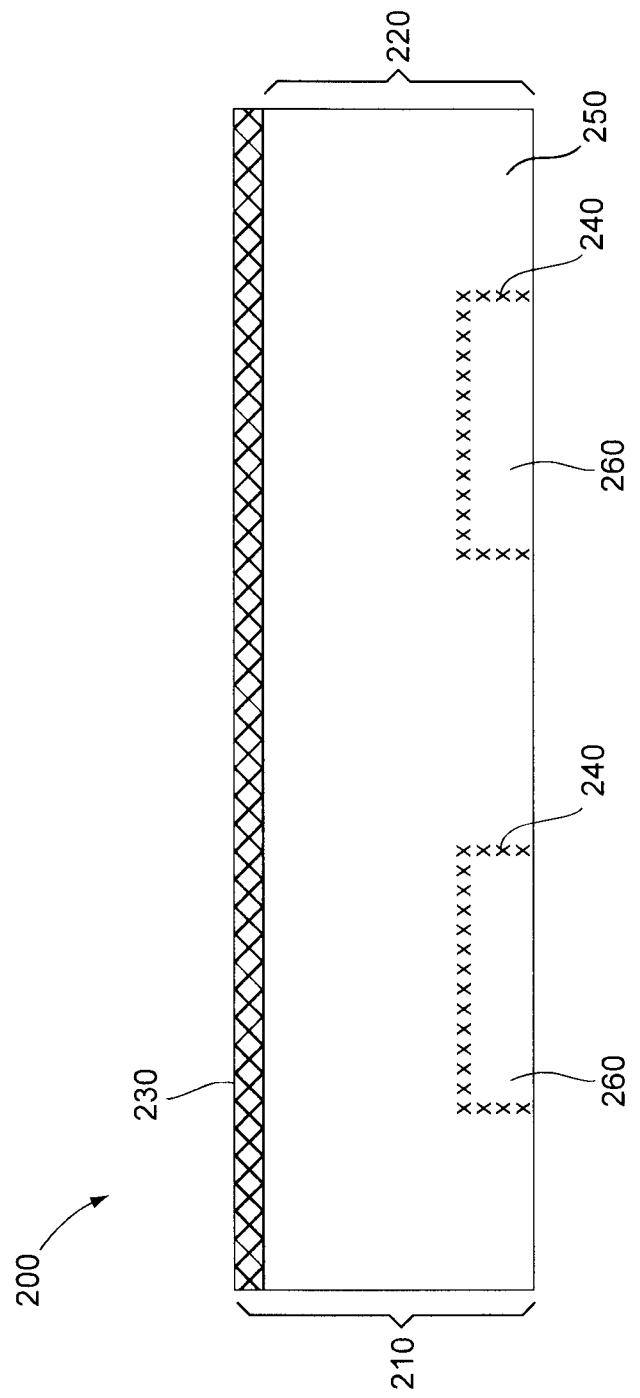
FIG. 5 shows a cross-sectional view of an exemplary composite nasal dilator wherein the spring element is derived in the base element through the interaction of two materials having physically or chemically differing characteristics.

Alternatively, as shown in FIG. 5, the spring element regions 240 along the base element 220 can be formed during an extrusion process of two or more materials, where a first material 250 is extruded and a at least a second material 260 having a different physical or chemical property than the first material 250 is coextruded with or injected into the first material 250 at particular spring element regions 240. For example, a first material 250 of the composite base element 220 can be extruded from a co-extrusion die, and then a second material 260 having differing physical or chemical properties can be co-extruded at certain time and space intervals during the process creating the spring element regions 240 within the base element 220. The at least two materials of the base element 220 are capable of interacting and imparting a desired spring effect along the spring element 240. In one embodiment, the at least two materials differ in hardness, creating a resistance to bending, and, as a result, a memory effect is created along the spring element regions 240 when the nasal dilator 200 is placed on a user's nose. In another embodiment, the at least two materials differ in a coefficient of expansion or cooling, that, when the materials differentially expand or contract, create a spring element 240 upon bending that imparts a resiliency and memory effect to the base element 220. In certain embodiments, at least one of the materials is a shrink material that, upon heating, shrinks and creates tension within the base element 220, creating a spring element 240. In one embodiment, the first material 250 is a heat shrink material. In one embodiment, the first material 250 has a three-dimensional shape with an elastic memory. In one embodiment, the second material 260 is a heat shrink material. In certain embodiments, the second material 260 has a three-dimensional shape with an elastic memory.

Figure 6:
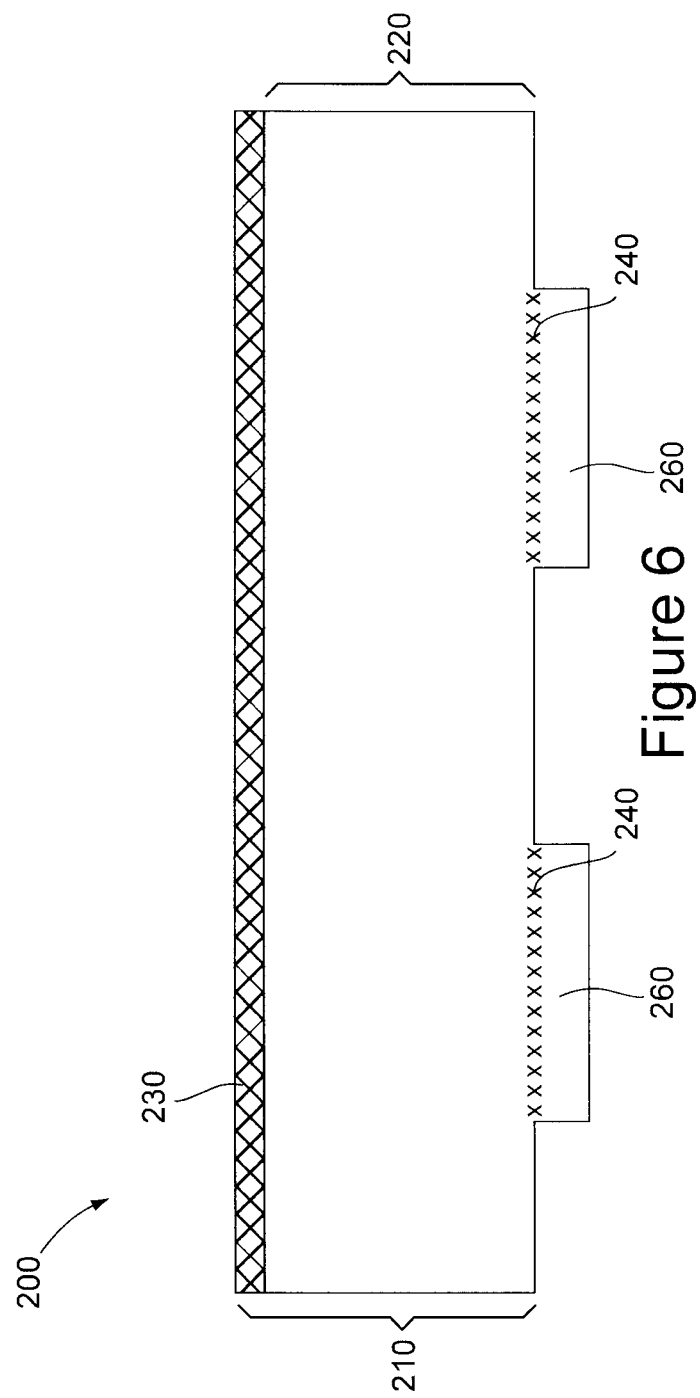
FIG. 6 shows a cross-sectional view of an exemplary composite nasal dilator wherein the spring element is derived at certain regions of the base element through the interactions of at least two materials having physically or chemically differing characteristics.

As shown in FIG. 6, the spring element 240 providing the nasal dilator 200 with flexibility and return memory properties towards a planar conformation may be imparted across certain regions of the base element 220 through the interaction of at least two materials having differing characteristics co-extruded or laminated during formation of the base element 220. In certain embodiments, the base element 220 is formed of at least two different materials, wherein at least one of the materials has a different physical or chemical property than one other material used to co-form the base element 220.

In one embodiment, the spring element regions 240 along the base element 220 can be formed during an extrusion process, where a first material 250 is extruded and at least a second material 260 having a different physical or chemical property than the first material 250 is coextruded with the first material 250 at particular spring element regions 240. For example, a first material 250 of the composite base element 220 can be extruded from a co-extrusion die, and then at least a second material 260 having differing physical or chemical properties can be co-extruded at certain time and space intervals during the process creating the spring element regions 240 within the base element 220. In an alternative embodiment, the spring element 240 can be induced within or across the base element 220 by laminating at least a first material 250 and a second material 260 having different chemical or physical properties, wherein the at least second material 260 is laminated at a position on a surface of the first material 250 that a spring element effect 240 is desired. The interaction between the first material 250 and second material 260 is capable of creating the spring element 240. In one embodiment, the at least two materials differ in hardness, creating a resistance to bending, and, as a result, a memory effect, at the spring element regions 240 when placed on the user's nose. In another embodiment, the at least two materials differ in a coefficient of expansion or cooling, resulting in a tension created at the spring element regions 240 upon bending that imparts a resiliency and memory effect to the base element 220. In certain embodiments, the base element 220 includes at least one material that shrinks or expands disproportionately when compared to at least one other material used to co-form the base element 220. In one embodiment, at least one of the materials is a shrink material and is coextruded with or laminated on another material along the desired spring element regions 240. In certain embodiments, the shrink material, upon heating, shrinks and creates tension within the base element 220, creating a spring element 240. In one embodiment, the first material 250 is a heat shrink material. In one embodiment, the first material 250 has a three-dimensional shape with an elastic memory. In one embodiment, the second material 260 is a heat shrink material. In certain embodiments, the second material 260 has a three-dimensional shape with an elastic memory.

Figure 7:
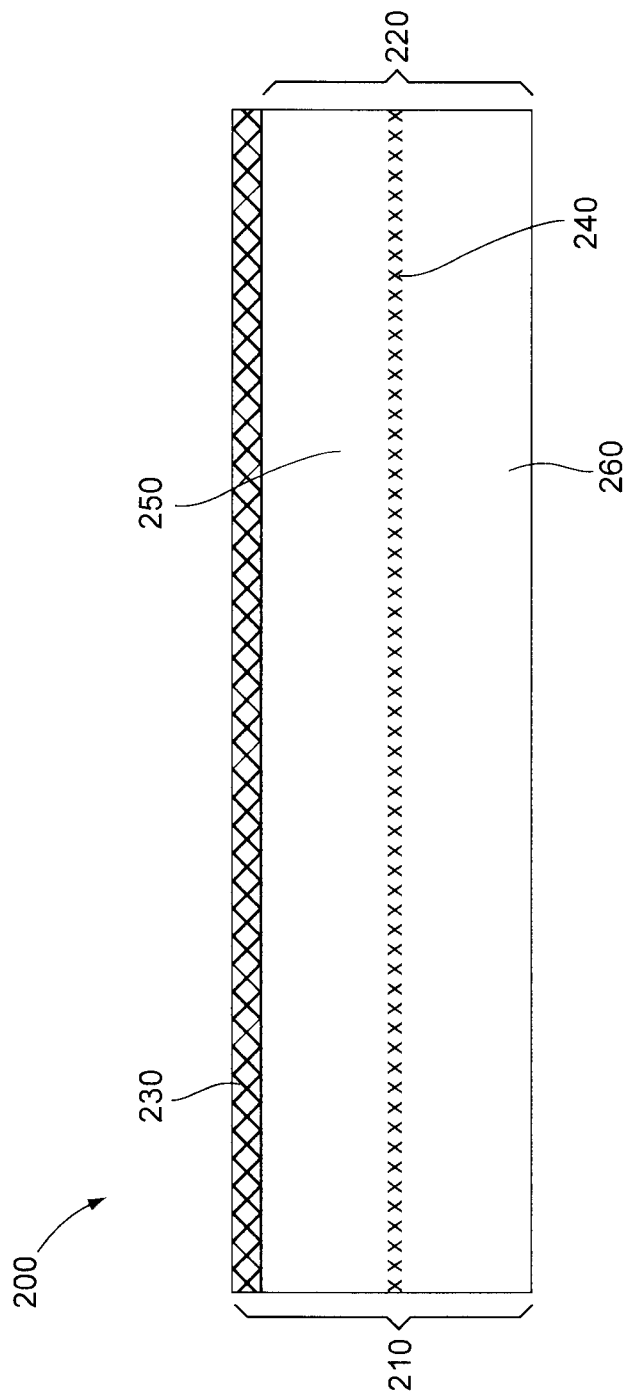
FIG. 7 shows a cross-sectional view of an exemplary composite nasal dilator wherein one or more spring elements are derived along the length of the base element through the interactions of at least two materials having physically or chemically differing characteristics.

In certain embodiments, as shown in FIG. 7, a spring elements 240 may be imparted along the longitudinal length of the base element 220, providing the base element 220 with flexibility and return memory properties towards a planar conformation. In certain embodiments, the base element 220 is co-formed of at least two materials having differing physical or chemical characteristics during an extrusion, wherein the interaction of the first material 250 and the second material 260 creates a spring element 240 along the longitudinal length of the base element 220. For example, the first material 250 of the base element 220 can be extruded from one co-extrusion die, while a second material 260 having differing physical or chemical properties is co-extruded during the process. The interaction of the first material 250 with the second material 260 is capable of creating a desired spring elements 240 across the length of the base element 220. In an alternative embodiment, the spring element 240 can be imparted into the base element 220 by laminating two materials having differing physical or chemical properties capable of interacting along their length to create a spring element 240 across the length of the base element 220. In one embodiment, the two materials differ in hardness, creating a resistance to bending, and, as a result, a memory effect, along the spring element 240 is created when placed on the user's nose. In another embodiment, the two materials differ in a coefficient of expansion or cooling, resulting in a tension created along the spring element 240 upon bending that imparts a resiliency and memory effect to the base element 220. In certain embodiments, the base element 220 includes a first material 250 or second material 260 that shrinks or expands disproportionately when compared to the other material. In one embodiment, a shrink material is coextruded with or laminated on another material at the desired spring element regions 240. In certain embodiments, the shrink material, upon heating, shrinks and creates tension within the base element 220, creating a spring element 240 upon bending. In one embodiment, the first material 250 is a heat shrink material. In one embodiment, the first material 250 has a three-dimensional shape with an elastic memory. In one embodiment, the second material 260 is a heat shrink material. In certain embodiments, the second material 260 has a three-dimensional shape with an elastic memory.

In one aspect of the invention, a method for manufacturing nasal dilators is provided. There are various methodologies of forming these nasal dilators, which may include steps such as: a) creating a composite base element having an outer surface and an inner surface, wherein the composite base material is comprised of at least two materials, two surfaces or two regions differing in at least one chemical or physical characteristic; and b) inducing a spring element in the base element through the interaction of the at least two materials, two surfaces or two regions. In certain embodiments, the spring element is induced along the interface of the two materials, two surfaces, or two regions within the base element due to a differential change in the materials, surfaces, or regions in response to physical conditions resulting in a permanent deformation of at least one of the materials, surfaces, or regions. In one embodiment, the differential change is due to differences in the coefficients of expansion, contractions upon cooling, or shrink properties of the materials, surfaces, or regions. In one embodiment, the differential change of is due to the differential loss of solvent, the differential absorption of solvent, the differential loss of moisture, or the differential absorption of moisture within the materials, surfaces, or regions, In certain embodiments, the spring element is induced through the chemical or physical treatment of the base element resulting in the permanent physical deformation of at least one of the materials, surfaces, or regions within the base element.

In one embodiment, the induction of the spring element results in the deformation of the base element from a linear shape so that the base element also deforms from a planar shape. The change in shape may cause controlled differential bending of the spring element resulting in the inner surface of the support film changing to a concave shape that will secure itself to the nose of the wearer by the adhesive, with controlled uplifting spring force. In certain embodiments, the change in shape may cause the base element to create tension in a direction opposite its position during use, creating control uplifting spring force on the nostrils during use. In certain embodiments, the change in shape may result in the development of a curvature along the longitudinal width of the nasal dilator, creating uplifting spring force during use. The impartation of curvature along the longitudinal width of materials is further described in U.S. Patent Publication No. 2009/0324883.

In certain embodiment, the nasal dilator is constructed on a base element and an adhesive layer. The base element has an elasticity built into it that will lift opposed sides of the nose by a spring or elastic action resulting in the desire of the base element to move from a curved shape over the nose during use towards a more linear form. By using differential properties in different materials of or regions within the base element, manufacturing steps previously used in the manufacture of nasal dilators can be eliminated, costs reduced, manufacture simplified, and properties tailored.

The present technology allows for simultaneous construction of all components of the base element and subsequent or simultaneous provision of the pressure-sensitive adhesive layer. One underlying element of technology described herein includes forming the base element by co-extrusion of two or more materials with differing characteristics, including different synthetic polymeric or composite materials, in appropriate orientation and layering that provides the ultimate desirable properties. Some essential properties (e.g., stiffness and memory) may be developed, activated or made latent in a single co-extrusion step by controlling the properties, compositions and additives in the various coextruded elements.

In one aspect of this invention, a nasal dilator can be manufactured using a co-extrusion system. A particularly useful co-extrusion system employs two or more extruders or multiple extrusion slots in the same extrusion head, such as that described in U.S. Pat. No. 5,725,814, each with a gear pump at its output connected to a co-extrusion die, allowing different materials to be extruded by each extruder. Varying the speed of one or both gear pumps varies the content of the extrudate. The gear pumps permit precise variation of the relative content of the materials extruded by the several extruders lengthwise along the extrudate. A display of a cross sectional dimension of the extrudate along a length of the extrudate permits observation of the lag that occurs between alteration of gear pump speed and the resultant change in dimension, so that a speed correction can be made at the appropriate time to correct or optimize for differing shrinkage and stretching characteristics between the several extruded materials in order to induce the desired characteristics within the extrudate.

During manufacture of the nasal dilators, in certain embodiments, the individual extruders feed to the die the base element materials, and, optionally, the adhesive layer, resulting in a single step, multiple material extrudate that forms the nasal dilator. The multiple extruders feeding the co-extrusion die can direct the layering and spatial placement of the various materials. For example, the die can layer the materials as follows: a first material comprising a non-shrink material is directed to the first layer of the extrudate. A second material comprising a shrink material is extruded simultaneously with the first material at desired spring element regions. The result is a two-layer, linear extrusion. In additional embodiments, a third material comprising a pressure sensitive adhesive can be coextruded on a surface of the first material opposite the surface that the second material interacts with.

In one embodiment, a co-extrusion system that employs two or more extruders, each with a gear pump as its output connected to a co-extrusion die by the use of gear pumps is used to produce the base element extrudate. Two or more extruders are employed in combination with a co-extrusion die and a gear pump is interposed between each extruder and the die. The amount of each material being delivered to the die is varied by controlling the speed of each gear pump. A gear pump is formed from two counter-rotating gears which are tightly meshed. The gear pump is used on the end of the extruder and acts as a metering pump to meter out a precisely measured amount of material. The gear pump can be thought of as a group of measuring cups on a wheel. The measuring cup—in this case the pocket between the teeth of the pump—is filled with material such as plastic melt at the input. It travels around the pump, getting leveled as it does so, so that the amount carried from input to output is precisely one tooth-full. At the output the gears mesh very closely, so the material cannot get back to the input, and so it exits. This type of pump is a positive displacement pump. The amount which exits is precisely proportional to the RPM of the pump to a very close tolerance, and the pump is relatively insensitive to such factors as viscosity, pressure, etc. Gear pump speed control will thus accurately control the rate of delivery of material to the die. By using gear pumps between the extruders and the die of a co-extrusion system, the amount of each constituent material at each location along the extrudate can be precisely controlled. In certain embodiments, three or more extruders or extrusion slots in a single extruder may be employed in combination with a co-extrusion die, which may allow the adhesive, which may include a pressure sensitive adhesive, to also be co-extruded.

In certain embodiments, for example, wherein the spring element is created only along certain portions of the base element, the base element can be manufactured by changing the speed of the extrudate of, for example, the second material from stopped to started at areas along the first material where the spring elements are desired, while simultaneously, slowing the speed of the extrudate of the first material.

In other embodiments, if the base element is to be made of more than one material, wherein the spring element is formed along the entire longitudinal length of the base element, the speeds of the gear pumps can be optimized to control for the potential shrink differences between the two materials, as different materials may shrink differently with changes in temperature and consequently the cross sectional dimensions of an extrusion may change as it changes from one material to another. Compensation for this can be made by an incremental change in one of the gear pump speeds.

Similarly, where stretch between the die and a puller varies from one material to another, tending to alter a cross sectional dimension, compensation can be effected in a system employing gear pumps by changing pump speed slightly, or in the case of a tube or blown film by correcting not only a pump speed, but air injected at the die.

In certain cases, a laser gauge downstream of the die can be used to detect variations in dimension. A sudden temporary gear speed change will show up on a monitor that displays cross sectional dimension. The lag, in terms either of time or length along the extrudate, is determined and the shrinkage or stretch compensating correction is made in advance of the extrusion of that portion of the extrudate requiring the correction. The time or distance in advance that the correction is made is the time or distance of the measured lag. Similarly, where air is used to control outside diameter a "blip" or sudden pulse of air is introduced and the line lag to the laser gauge is noted, whereupon a correcting air input can be subsequently made at the correct location.

Using a co-extrusion system, the thickness of each of the layers of the extrudate is proportional to the amount of material which goes into each of the inputs of the die, and can be controlled. Furthermore, changes to the composition of the extrudate can be controlled, allowing differential material to be used along the extrudate, providing for the switching back and forth between desired characteristics of the base element along a longitudinal axis.

In one aspect of the invention, a continuous process for manufacturing nasal dilators is provided comprising: (a) extruding a first material having a first surface and a second surface from a co-extrusion die; (b) extruding a second material having a first surface and a second surface from a co-extrusion die, wherein the first material and the second material comprise a base element, and wherein the first material and second material have different chemical or physical properties, wherein the interaction of the first material and the second material at their interface creates a spring element into the base element; wherein the second material is extruded into or on at least one portion of one surface of the first material. In certain embodiments, the second material is a shrink material. In certain materials, the second material shrinks when exposed to heat. In certain embodiments, the process further includes exposing the extrudate to heat in order to shrink the second material, creating a spring element along the interface of the first and second materials. In certain embodiment, the process further includes extruding a third material onto a surface of the first material opposite the second material, wherein the third material comprises an adhesive, such as a pressure sensitive adhesive. In certain embodiments, the process can further include laminating or temporarily adhering a release liner or a release paper strip, such as silicone or wax coated kraft paper, over the pressure sensitive adhesive layer. This can be done according to standard manufacturing techniques, wherein after or during application of the adhesive, the release sheet is placed against the adhesive layer, usually by unrolling a stored release sheet.

Similarly, the base element can be derived through a lamination of two or more materials with differing properties in an appropriate orientation to provide the desirable characteristics. The co-formed base element materials act in concert to allow for sufficient flexibility in the nasal dilator structure to conform to the curvature over a human nose, and then to provide such sufficient elastic memory in attempting to return towards a planar orientation of the base element so as to lift outer surfaces of the nose and dilate nasal passages by the lifting action. Preformed adhesive layers (e.g., thermal adhesive layers, water-activated adhesive layers and the like) may be laminated to the base element. Application of these layers may also be provided by extrusion of the adhesive layer through slots or die heads onto the previously formed base element.

In one aspect of the invention, a continuous process for manufacturing nasal dilators is provided comprising: (a) providing a first material having a first surface and a second surface; (b) laminating a second material having a first surface and a second surface on at least one portion of the first material, the second material having different chemical or physical properties than the first material, wherein the interaction along the interface of the first material and the second material creates a spring element in the base element. In certain embodiments, the second material has a three-dimensional shape with an elastic memory. In certain embodiment, the process further includes disposing a third material onto a surface of the first material opposite the second material, wherein the third material comprises a pressure sensitive adhesive. In certain embodiments, the process can further include laminating a release paper strip, such as silicone or wax coated kraft paper, over the pressure sensitive adhesive layer. In certain embodiments, the spring element is induced along the interface of the first material and second material within the base element due to differential changes in the two materials in response to physical conditions. In one embodiment, the differential change is due to differences in the coefficients of expansion, contractions upon cooling, or shrink properties of the first material and second material. In one embodiment, the differential change of the two materials is due to the differential loss of solvent, the differential absorption of solvent, the differential loss of moisture, or the differential absorption of moisture. In certain embodiments, the spring element is induced through the chemical or physical treatment of the base element resulting in the permanent physical deformation of at least one of the materials. In certain embodiments, the first, second, or both materials shrink when exposed to heat. In further embodiments, the process further includes exposing the laminate to heat in order to shrink the first or second material. The laminate materials can be provided on rolls, and adhesively joined together in a webbing operation.

When the two materials used to create the spring element have differential shrink properties, differential contraction properties, or differential expansion properties, the application of thermal energy (by conductive or convective heating, IR radiation, and the like) will cause the two layers to shrink and/or expand at different rates. Particularly when there is a persistence or permanent change caused by shrinkage, contraction, or expansion (e.g., as with a heat shrink material being one of the components, layers or films), the differential in dimensions caused by shrinkage and/or expansion causes the base element to arc or curl, with the "shorter" or greater shrinking component being on the concave side of the arc and the "longer" or less shrinking component being on the convex side of the arc. It is preferred that the thermal treatment create a permanent memory of the dimensional change as by heat shrinkage, heat contraction, or heat relaxation of the material, as is known to occur in the classes of shrink materials discussed and described herein.

Other materials may also be included in the nasal dilator. For example, an adhesive layer or tie layer for assisting in bonding the differing materials of the composite base element can be coextruded between the at least first material and second material, or in the case of a lamination, disposed on a surface of one of the materials, if needed so improved adhesion between the materials occurs. Tie layers, for example, can be single components or multiple component compounds. Typical compounds for this use including maleic anhydride modified elastomers, ethyl vinyl acetates and olefins, polyacrylic imides, butyl acrylates, peroxides such as peroxypolymers, e.g., peroxyolefins, silanes, e.g., epoxysilanes, reactive polystyrenes, chlorinated polyethylene, acrylic acid modified polyolefins and ethyl vinyl acetates with acetate and anhydride functional groups and the like, which can also be used in blends or as compatiblizers in one or more of layers. Tie layers are sometimes useful when the bonding force between the two materials is low. Adhesives can be, for example, in the form of a water-based adhesive, solvent-based adhesive, solvent-less adhesive, 100% solids adhesive, or hot melt adhesive. Such adhesives, for example, can be acrylic based, rubber based, or silicone based, and can include, for example, polyacrylates, thermoplastic acrylic solutions, thermal curing acrylics, self-curing or ambient temperature acrylics, 100% solid thermoplastic acrylics, vinyl alkyl ether, polyurethane-polyethylene adhesives, styrene-diene block copolymers, two component adhesives, such as polyurethane and polyethylene based adhesives, an crosslinking type adhesives. Examples of potential acrylic adhesive components include homopolymers or copolymers of a (meth)acrylic acid alkyl ester, for example (meth)acrylic acid $C_1$-$C_{20}$ alkyl ester such as methyl (meth)acrylate, ethyl (meth)acrylate, butyl (meth)acrylate, 2-ethylhexyl (meth)acrylate, and octyl (meth)acrylate; and copolymers of the above-described (meth)acrylic acid alkyl ester and another copolymerizable monomer including a carboxyl group-containing or acid anhydride group-containing monomer such as acrylic acid, methacrylic acid, itaconic acid, fumaric acid or maleic anhydride; a hydroxyl group-containing monomer such as 2-hydroxyethyl (meth)acrylate; an amino group-containing monomer such as morpholyl (meth)acrylate; an amide group-containing monomer such as (meth)acrylamide; a cyano group-containing monomer such as (meth)acrylonitrile; or a (meth)acrylic acid ester having an alicyclic hydrocarbon group such as isobornyl (meth)acrylate.

The acrylic adhesive polymer can include a copolymer of one or more of (meth)acrylic acid $C_1$-$C_{12}$ alkyl esters such as ethyl acrylate, butyl acrylate or 2-ethylhexyl acrylate, and at least a copolymerizable monomer selected from hydroxyl group-containing monomers such as 2-hydroxyethyl actylate and a carboxyl group-containing or acid anhydride group-containing monomer such as acrylic acid, or a copolymer of one or more of (meth)acrylic acid $C_1$-$C_{12}$ alkyl esters, a (meth)acrylic acid ester having an alicyclic hydrocarbon group, and at least a copolymerizable monomer selected from hydroxyl group-containing monomers and carboxyl group-containing or acid anhydride group-containing monomers.

The acrylic polymer is, for example, prepared by photopolymerizing (for example, with an ultraviolet light) the monomer components described above (and polymerization initiator) in the absence of solvent, as a liquid prepolymer of a high viscosity. Furthermore, a crosslinking agent can be added to the prepolymer. The crosslinking agent may be added at the preparation of the prepolymer. The crosslinking acrylic adhesive composition may also be obtained by adding, to an acrylic polymer obtained by polymerizing the monomer components described above or a solution thereof, a crosslinking agent and a solvent (not essential in a case of utilizing the solution of the acrylic polymer).

The crosslinking agent is not particularly restricted, and, for example, an isocyanate type crosslinking agent, a melamine type crosslinking agent, an epoxy type crosslinking agent, an acrylate type crosslinking agent (polyfunctional acrylate), or a (meth)acrylic acid ester having an isocyanate group may be used for this purpose. Examples of the acrylate type crosslinking agent include hexanediol diacrylate, 1,4-butanediol diacrylate, trimethylolpropane triacrylate, pentaerythritol tetraacrylate, and dipentaerythritol hexaactylate. Examples of (meth)acrylic acid ester having an isocyanate group include 2-isocyanatethyl acrylate and 2-isocyanatethyl methacrylate. The crosslinking agent is normally employed in an amount of from 0.01 to 15 parts by weight with respect to 100 parts by weight of the base polymer.

The crosslinking acrylic adhesive may contain, in addition to the base polymer and the crosslinking agent, appropriate additives such as a crosslinking promoter, a tackifier resin (such as a rosin derivative resin, a polyterpene resin, a petroleum resin, or an oil-soluble phenolic resin), a viscosifier, a plasticizer, a filler, an aging resistor, and an antioxidant.

One particular advantage of the continuous process to create a nasal dilator described above is that the resultant extrudate or laminate can be produced in a single, continuous, linear extrusion or laminating step. As such, the nasal dilator intended for use can be die cut from a continuously provided liner sheet or web of extrudate or laminate.

Figure 8:
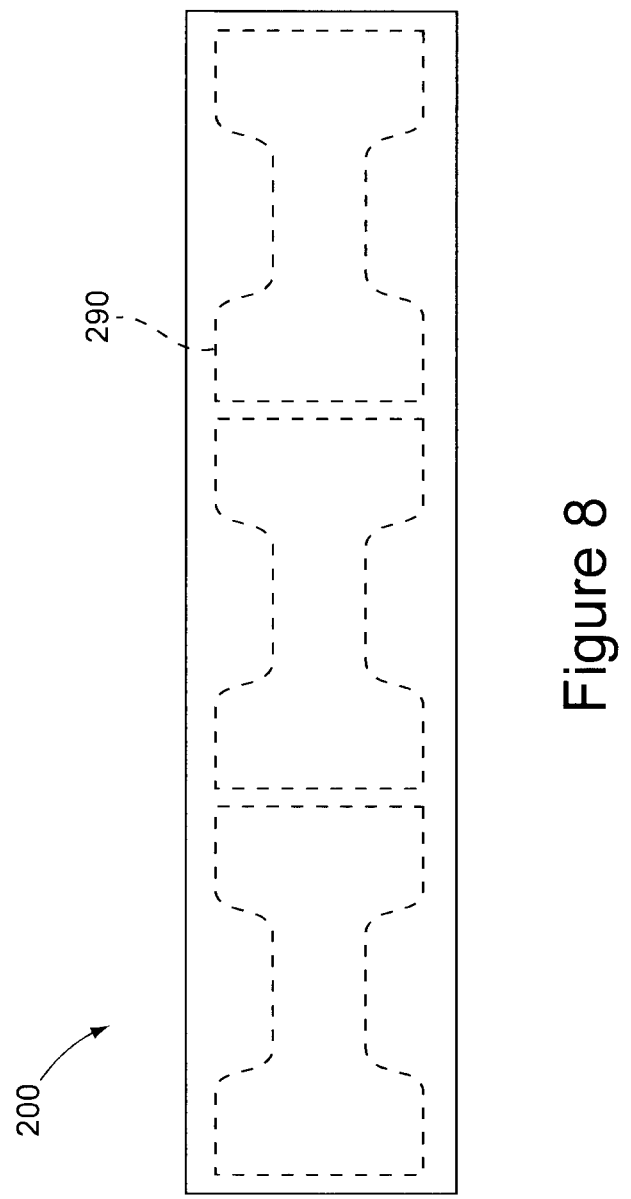
FIG. 8 shows a frontal cropped view of an unfurled roll of a resultant composite nasal dilator extrudate or laminate with die cut perforations in the shape of the nasal dilator.

In one embodiment, the resultant extrudate or laminate web or sheet is perforated and formed into a roll. Shown in FIG. 8 is a cropped view of an unfurled roll of a resultant extrudate or laminate that has a perforation 290 in the shape of the nasal dilator 200. The perforation can be imparted by a die-cut. The perforation facilitates the removal of each nasal dilator 200 from the roll to permit individual application and use. As such, the nasal dilator can be dispensed as a continuous roll having die cut perforations as separations. The user simply removes the nasal dilator from the roll at the die cut perforations, removing the liner if provided, and affixes the nasal dilator across the nose.

In certain embodiments, the materials used to form the spring element of the current invention can broadly include, but are not limited to, any material which is capable of being formed into thin films and exhibits elastomeric properties at ambient conditions. Elastomeric means that the material will substantially resume its original shape after being flexed, stretched, or bent. In certain embodiments, the materials used to form the spring element are heat-shrinkable elastics. Such materials are particularly attractive due to the ability to be fabricated into the base element. For example, using an unstable stretched shrink-material at ambient conditions and then later applying heat to shrink the material results in a tension between the shrink material and at least one other material used in the base element along the interface of the shrink material and one other material, providing for resiliency in the base element, allowing the base element to be flexible, and providing the base element with return memory properties towards a planar conformation. In certain embodiments, the heat shrink materials used preferentially shrink along the longitudinal axis of the base element, resulting in tension being applied along the interface of the shrink material, and when bent, creating lift at the ends of the nasal dilator as the base element seeks a return to planar conformation upon application to the user's nose.

To create a shrink material, the material may be heated within its orientation temperature range (which varies according to the material's composition, but is usually and preferably above room temperature) and below the material's melting temperature. After being stretched, the material can be rapidly cooled; such rapid cooling or quenching freezes the shrink material molecules in their oriented state. Upon sufficient heating, the orientation stresses are released, and the shrink material will begin to shrink back to its original un-oriented dimension.

For example, PVC and polyolefin shrink materials provide a wide range of performance characteristics, such as shrink force (the amount of force that a material exerts per unit area of its cross-section during shrinkage), degree of free shrink (the reduction in surface area a material undergoes when unrestrained), tensile strength (the highest force that can be applied to a unit area of material before it begins to break), sealability, shrink temperature curve (the relationship of shrink to temperature), tear initiation and resistance (the force at which a material will begin to tear and continue to tear), optics (gloss, haze and transparency of material), and dimensional stability (the ability of the film to retain its original dimensions under all types of storage conditions).

Shrink material characteristics play an important role in selecting a particular shrink material and may differ for different desired characteristics or equipment. Consideration must be given to the amount of tension and elasticity desired to be created, the non-shrink materials used, and the strength of the pressure sensitive adhesive used to adhere the nasal dilator on the user's nose.

Although specific materials, dimensions, temperatures and apparatus are described in this document, those specific disclosures are intended to be merely examples of the generic concepts described and claimed herein.

What is claimed:
1. A nasal dilator comprising:
a composite base element comprising a first material and a second material;
wherein the first material in the composite base element comprises a heat activated polymeric shrink film, wherein heat activation of the polymeric shrink film occurs at a temperature above ambient temperature, and wherein the heat activated polymeric shrink film shrinks at a greater ratio than the second material upon heat activation;

wherein the differential in shrink ratio between the first and second material induces a spring element within the composite base element which imparts resiliency into the composite base element and provides the composite base element with elastic memory properties towards a planar conformation during use;

wherein the elastic memory is not substantially altered upon exposure to ambient temperature;

the composite base element having an outer surface and an inner surface, the inner surface of the composite base element having a pressure-sensitive adhesive disposed thereon suitable for adhering the nasal dilator to a user's nose; and wherein the spring element is present in the composite base element prior to the adherence of the nasal dilator to the user's nose.

2. The nasal dilator of claim 1, wherein the first material of the base element is located on the outer surface of the base element.

3. A nasal dilator comprising:
a. a composite base element comprising at least a first material and a second material, wherein at least one of the materials is a polymeric shrink film which contracts in a disproportionate ratio compared to the other material when exposed to heat, wherein the contraction induces a spring element within the composite base element which imparts resiliency into the composite base element and provides the composite base element with elastic memory properties towards a planar conformation during use;
b. the composite base element having an outer surface and an inner surface, the inner surface of the composite base element having a pressure-sensitive adhesive disposed thereon suitable for adhering the nasal dilator to a user's nose;

wherein the spring element is present in the composite base element prior to the adherence of the nasal dilator to the user's nose.

4. The nasal dilator of claim 3, wherein the heat activation occurs above ambient temperature.

5. The nasal dilator of claim 1, wherein the first material comprises a polyester.

6. The nasal dilator of claim 5, wherein the polyester is a polyethylene terephthalate.

7. The nasal dilator of claim 1, wherein the second material comprises a polyester.

8. The nasal dilator of claim 7, wherein the polyester is a polyethylene terephthalate.

9. The nasal dilator of claim 1, wherein the first material has a longitudinal length and longitudinal width, wherein, upon heat activation, the first material contracts along its longitudinal length.

10. The nasal dilator of claim 1, wherein the first material has a longitudinal length and longitudinal width, wherein, upon heat activation, the first material contracts along its longitudinal width.

11. The nasal dilator of claim 3, wherein the polymeric shrink film comprises a polyester.

12. The nasal dilator of claim 11, wherein the polyester is polyethylene terephthalate.

13. The nasal dilator of claim 11, wherein both the first material and the second material comprises a polyester.

14. The nasal dilator of claim 13, wherein the polyester is polyethylene terephthalate.

15. The nasal dilator of claim 3, wherein the polymeric shrink film has a longitudinal length and a longitudinal width, wherein, upon heat activation, the polymeric shrink film contracts along its longitudinal length.

16. The nasal dilator of claim 3, wherein the polymeric shrink film has a longitudinal length and a longitudinal width, wherein, upon heat activation, the polymeric shrink film contracts along its longitudinal width.

* * * * *